United States Patent [19]

Batz et al.

[11] 4,337,310

[45] Jun. 29, 1982

[54] METHOD FOR THE DETERMINATION OF α-AMYLASE

[75] Inventors: Hans-Georg Batz, Tutzing; Elli Rauscher, Munich; Gunter Weimann, Tutzing; August W. Wahlefeld, Weilheim; Wolfgang Gruber, Tutzing-Unterzeismering, all of Fed. Rep. of Germany

[73] Assignee: Boehringer Mannheim GmbH, Mannheim-Waldhof, Fed. Rep. of Germany

[21] Appl. No.: 184,675

[22] Filed: Sep. 8, 1980

Related U.S. Application Data

[63] Continuation of Ser. No. 29,814, Apr. 13, 1979, abandoned.

[30] Foreign Application Priority Data

May 2, 1978 [DE] Fed. Rep. of Germany ....... 2819298

[51] Int. Cl.³ .............................................. C12Q 1/40
[52] U.S. Cl. ...................................... 435/22; 536/106
[58] Field of Search ................. 23/230 B; 252/408 R; 106/213, 214; 435/22; 536/47, 106

[56] References Cited

U.S. PATENT DOCUMENTS

| | | | |
|---|---|---|---|
| 2,500,950 | 3/1950 | Konigsberg | 536/106 |
| 3,525,672 | 8/1970 | Wurzburg et al. | 536/106 |
| 3,597,322 | 8/1971 | Babson | 435/22 |
| 3,759,794 | 9/1973 | Sax et al. | 435/22 |
| 4,025,392 | 5/1977 | Dougherty | 435/22 |

FOREIGN PATENT DOCUMENTS

| | | |
|---|---|---|
| 1901517 | 7/1970 | Fed. Rep. of Germany . |
| 1668515 | 10/1970 | Fed. Rep. of Germany . |
| 1333420 | 10/1973 | United Kingdom ............ 252/408 R |

OTHER PUBLICATIONS

Ewen, "Synthesis of Cibachron Blue F3GA-Amylose, *Clinica Chimica Acta*, Aug. 30, 1973, pp. 233–248.

Primary Examiner—Peter A. Hruskoci
Attorney, Agent, or Firm—Felfe & Lynch

[57] ABSTRACT

Method for Determining α-amylase by incubating with a starch substrate, wherein the substrate is based upon particulate starch derivatized with detectable groups for the determination of α-amylase, the substrate consisting of superficially cross-linked starch or amylose grains having a regulated, reduced swellability, said grains having a diameter of from 0.01 to 0.20 mm; these grains are prepared by suspending non-swollen grains in a solution with only enough cross-linking agent to achieve superficial cross-linking and then derivatizing the grains with the detectable groups for the determination of α-amylase.

3 Claims, 1 Drawing Figure

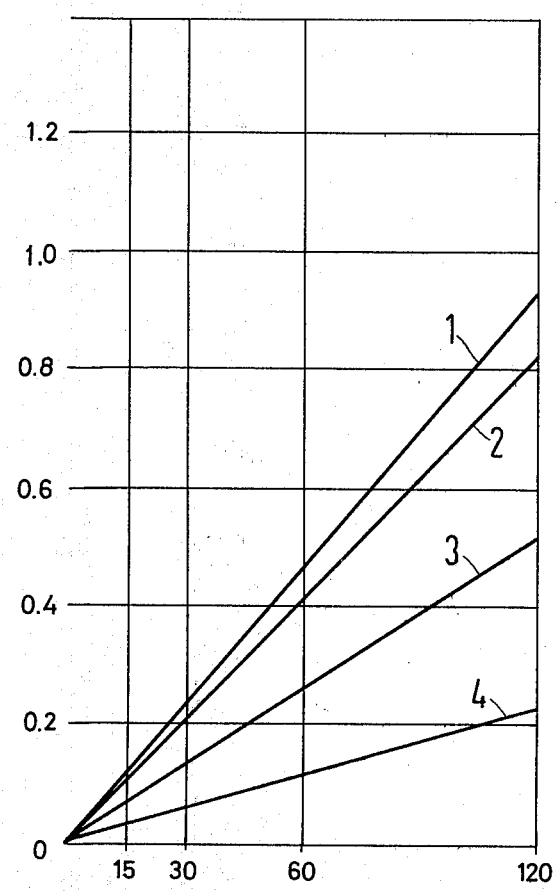

METHOD FOR THE DETERMINATION OF α-AMYLASE

This is a continuation of application Ser. No. 29,814, filed Apr. 13, 1979, now abandoned.

The present invention is concerned with a method for determination of α-amylase.

The determination of the α-amylase level in serum is an important clinical parameter for pancreatic function.

The inventive method is based on the ability of α-amylase to split the 1,4-glycosidic bond of starch and starch derivatives. The enzymatic attack does not necessarily take place from the end of the chain, it can also commence in the middle of the chain of a cross-linked starch molecule. Insoluble starch is hereby split into soluble starch fragments and unbranched chains are finally split to give maltose. The rate with which this decomposition takes place is a measure of the amount of amylase present. If dyed, insoluble starch is used, then colored soluble fragments are obtained and the degree of fission can thus be determined from the resulting color of the solution (see Experientia 23, 805/1967). As dyestuffs for this purpose, it has been suggested to use reactive dyestuffs, such as are also used for dyeing cellulose fibres.

Since, however, starch is not absolutely insoluble and, therefore, can only be worked up with difficulty (for example, by dyeing), it was suggested in German Patent Specification No. 1,901,517 to prepare an absolutely insoluble gel by cross-linking soluble starch, for example with epichlorohydrin, and then to comminute and dye it.

The exactitude of this amylase determination system ultimately depends upon the fact that such a large excess of the substrate is provided for the enzyme that even after ending (stopping) the reaction, excess substrate is present, i.e. enzyme can always exert an optimum splitting action during the reaction. However, this also means that, for comparable measurements, there must be provided not only the same amount of substrate but also a comparatively large surface area of the substrate, as well as a comparable and uniform meshwork. In the case of the substrate described in Federal Republic of Germany Patent Specification No. 1,901,517, the amylase is admittedly provided with comparable surface areas per unit weight (by breaking up the gel into approximately equal pieces by means of a sieve) but a degree of cross-linking which is always uniform cannot be achieved reproducably since, on the one hand, in the case of the fission of the starch, which itself is already non-uniform, there is obtained a mixture of soluble starch fragments having, on average, different lengths from batch to batch and, on the other hand, in the case of subsequent cross-linking, due to the so-called Trommsdorf effect, a non-uniformly cross-linked product is to be expected.

The Trommsdorf effect describes the auto-accelerating cross-linking reaction proceeding exothermally due to loss of entropy which can only be kept under control with difficulty.

For these reasons, the substrate produced as described above differs from batch to batch. Problems also arise with the linearity of the absorption in the case of increasing enzyme concentration (see Clin. Chim. Acta, 47, 233/1973). Therefore, a calibration curve must be produced for each packing, which means an additional expense.

The present invention substantially overcomes the disadvantages of these known cross-linked substrates for α-amylase based upon starch and provides a substrate which is substantially more uniform not only within one batch but also from batch to batch, i.e., gives a better linearity of the absorption and makes unnecessary the production of new calibration curves.

The substrate of the present invention is based upon particulate starch derivatized with determinable groups for the determination of α-amylase, wherein the substrate consists of superficially cross-linked starch or amylose grains with a regulated, reduced swellability, said grains having a diameter of from 0.01 to 0.20 mm.

The cross-linking of non-gelatinized starch with the help of ether-forming agents is already known from U.S. Pat. No. 2,500,950. The products described therein are said to be useful as foodstuffs, as well as for textile finishing. From Federal Republic of Germany Patent Specification No. 1,668,515, it is also already known to break down starch grains, the swellability of which has been inhibited by cross-linking, with β-amylase, α-1,4-glucosidase or phosphorylase in order to obtain a starch decomposition product which, as a component of tinned foodstuffs, imparts an improved low temperature stability thereto. Any indication that superficially cross-linked, derivatised starch or amylose grains of the above-given diameter are especially uniformly attacked by α-amylase and can, therefore, be used for analytical purposes, cannot be deduced therefrom. Surprisingly, the inherently inhomogeneous starch yields, after the cross-linking, due to swelling, a substrate which is substantially more uniformly decomposed and, therefore, possesses a superior suitability as a substrate for α-amylase. It is assumed that the already cross-linked amylopectin cover in the outer part of the starch grain is strengthened by the process described in detail hereinafter so that the α-amylase is provided with a substrate which cannot undergo normal swelling and is thus subject to a certain internal pressure.

Thus to a preferred embodiment of the present invention α-amylase is incubated with a substrate consisting of starch grains which are cross-linked with 0.0009 to 0.0027 mole of a difunctional cross-linking agent per 100 g. of non-swollen starch grains, non-swollen grains with a diameter of from 0.01 to 0.1 mm. having proved to be particularly useful.

According to a further preferred embodiment of the present invention, the substrate consists of amylose grains which are cross-linked with 0.02 to 0.07 mole of a difunctional cross-linking agent per 100 g. non-swollen amylose grains, those amylose grains having been found to be especially useful which have a diameter of from 0.05 to 0.20 mm.

The process according to the present invention for the preparation of starch or amylose in the form of grains with regulated, reduced swellability by cross-linking swollen starch with a difunctional cross-linking agent in aqueous medium starts from non-swollen starch or amylose grains with a diameter of from 0.01 to 0.20 mm. which are suspended in a solution with a content of cross-linking agent which is only sufficient for superficial cross-linking until the cross-linking agent is used up, whereafter the grains are derivatised with determinable groups in known manner.

Examples of difunctional cross-linking agents which can be used include aliphatic halides, such as propylene dichloride, dichloropentane, ethylene dibromide, glycerol dichlorohydrin and dichlorobutane; ether-forming epoxyhalogen compounds, such as epichlorohydrin and epibromohydrin; cyanuric chloride; phosphorus oxychloride; metaphosphates and polymetaphosphates; aldehydes, such as formaldehyde, glutardialdehyde and acrolein; succinic acid anhydride and the like.

As already mentioned above, when applying the process to starch grains, an amount of cross-linking agent of from 0.0009 to 0.0027 mole per 100 g. of non-swollen starch grains is used, the diameter of these grains thereby being most advantageously from 0.01 to 0.1 mm. On the other hand, in the case of amylose grains, the best results are achieved with 0.02 to 0.07 mole of cross-linking agent per 100 g. non-swollen amylose grains, the latter best having a diameter of from 0.05 to 0.20 mm. The differences in the amount of cross-linking agent used depend upon the fact that, in the case of starch grains, the natural amylopectin cover is itself already cross-linked and, therefore, for the achievement of the desired reduced swellability, relatively little cross-linking agent is necessary. In the case of too small an amount of cross-linking agent, the swellability is too great, whereas in the case of too high an amount of cross-linking agent, the grains become too stable and sufficient free amylose chains are no longer present for attack by the $\alpha$-amylase. On the other hand, amylose is ab initio not cross-linked so that, for the preparation of the substrate according to the present invention, more than 10 times as great an amount of cross-linker is used. Whereas, in the case of starch, according to the present invention, the swelling is retarded, in the case of the crystalline amylose grains, which are insoluble in cold water, it is only by means of the cross-linking that swellable products are obtained at all. Since, in the case of technical amylose, certain amounts of amylopectin are frequently still present, it is preferable to determine the amylopectin content and to calculate therefrom the necessary amount of cross-linker.

The determinable groups with which the substrate is derivatised are preferably dyestuff or dyestuff-forming groups, i.e. those which are subsequently reacted with a further component to give a dyestuff. The dyestuffs can absorb in the visible light or at non-visible wavelengths. Fluorescent dyestuffs can also be used. Furthermore, radioactive or enzymatically-determinable groups can be introduced. Cibacron Blue 3 GA has proved to be especially useful. Dyestuffs containing a diazo system have proved to be unsuitable because of their exchange action with polysaccharides, as well as their hydrophobic properties.

Apart from the above-described preferred dye-stuff, other chemically similar dyestuffs have also proved to be very useful but, in practice, they often contain naphthalenesulphonic acid as additive and the latter inhibits $\alpha$-amylase, even in very small amounts.

In the case of other determinable groups, too, which, from the aspect of the chemical structure, can be used for the derivatisation of the substrate, it is important that they do not inhibit the $\alpha$-amylase itself which, in every case, can easily be ascertained by a simple preliminary experiment. Derivatisation itself is carried out in known manner, for example, by methods used in cotton dyeing, and does not need to be described here in detail.

The substrate according to the present invention for the $\alpha$-amylase determination is preferably employed in an amount of from about 5 mg./ml. to 150 mg./ml. Amounts are especially preferred from about 20 to about 50 mg./ml. since hereby, under all conditions, i.e. also in the case of pathological sera, a sufficiently large excess of substrate is available.

In the accompanying drawing, two reagents according to the present invention are compared with two commercially available amylase substrates based on dyed starch, with regard to the extinction developed per unit time in the case of the same amounts of substrate and also under otherwise identical conditions. Curve 1 is a substrate according to the present invention based upon starch, curve 2 is a substrate according to the present invention based upon amylose, curve 3 is a commercially available substrate which was prepared by cross-linking soluble starch and subsequent dyeing and curve 4 is another commercially available substrate of other origin which, in principle, was prepared similarly to the substrate of curve 3. All four substrates were dyed with Cibacron Blue 3 GA.

The curves illustrated in the accompanying drawing were obtained by incubating 5.0 ml. amounts of a 10% substrate suspension with 100 $\mu$l. $\alpha$-amylase standard at 30° C. At definite times, 1.0 ml. 0.5 N aqueous sodium hydroxide solution was added thereto, filtered and the extinction E 578 measured at n=2 against air. As the accompanying drawing shows, in the case of the substrates according to the present invention, at about the same blank value as the comparison substrates show it, an almost double so high extinction is achieved.

The following Examples are given for the purpose of illustrating the present invention:

EXAMPLE 1

Preparation of $\alpha$-amylase substrate from potato starch 16 g. sodium hydroxide are introduced, with stirring, into 6 liters water, then 1000 g. starch (average grain size 0.01 to 0.1 mm., sieved) are stirred in and 2 ml. epichlorohydrin slowly added dropwise. The batch is stirred for 15 hours at ambient temperature, thereafter adjusted to pH 7 to 8 with 2 N hydrochloric acid (about 200 ml. 2 N HCl) and left to stand for about 1 hour. The cross-linked starch thereby deposits and the slightly turbid supernatant is decanted off and discarded. The remaining 2 to 3 liters are introduced, with vigorous stirring, into about the 5 fold amount of methanol. The suspension is further stirred for 1 hour and the precipitate is then filtered off with suction and dried in a vacuum at ambient temperature. Yield: 0.8 to 1 kg.

Dyeing is carried out as follows: 6 kg. anhydrous sodium sulphate are dissolved, with stirring and heating, in 30 liters of water, then heated to 98° C. and 1 kg. of the cross-linked starch introduced portionwise. 0.4 kg. of dyestuff Cibacron Blue 3 GA are then added thereto, whereafter the solution is kept at this temperature for a further 10 minutes. 0.92 kg. Sodium phosphate dodecahydrate are then added thereto, whereafter the solution is again stirred for 15 minutes at 95° to 98° C. Thereafter, it is left to cool and deposit. The batch is filtered off or centrifuged off and washed until the filtrate is colourless. The swollen, water-containing product is then introduced, with vigorous stirring, into about the 5 fold amount by volume of methanol. The resulting suspension is further stirred for 1 hour and subsequently filtered off with suction. It is then washed with acetone and dried in a vacuum at ambient temperature. Yield: 1.0 to 1.1 kg. of dyed, cross-linked starch.

EXAMPLE 2

Preparation of α-amylase substrate from amylose

The procedure described in Example 1 is repeated but, instead of starch, there are used 1000 g. amylose with an average grain diameter of from 0.05 to 0.20 mm. (sieved) and 25 ml. epichlorohydrin.

EXAMPLE 3

Carrying out an α-amylase determination

| Reagents | concentrations |
|---|---|
| suspension of the substrate | 20 mg./ml. in sodium phosphate buffer 20 mmole/l containing sodium chloride 50 mmole/l pH 7.0 |
| aqueous sodium hydroxide solution | 0.5 mole/l |
| measurement conditions: | |
| incubation temperature: | 30° C. |
| incubation time: | 15 minutes |
| measurement wavelength: | 578 nm (550 to 650 nm) |
| layer thickness: | 1 cm. |
| Reagent blank value: instead of sample, distilled water is used. | |
| Pipette into the reaction vessel: | |
| suspension (30° C.) | 5.0 ml. |
| sample | 0.1 ml. |
| mix, incubate for precisely 15 minutes at 30° C. Stop the reaction by the addition of: | |
| 0.5N aqueous sodium hydroxide solution | 1.0 ml. |
| filter through a fluted filter (possibly centrifuge and carefully pour off). Measure the extinction of the supernatant against the reagent blank value (RBV). | |
| $E_{sample} - E_{RBV} = \Delta E$ Evaluation via colour or enzyme standard solution. | |

It will be understood that the specification and examples are illustrative but not limitative of the present invention and that other embodiments within the spirit and scope of the invention will suggest themselves to those skilled in the art.

What is claimed is:

1. Method for the determination of alpha-amylase in serum comprising incubating for a precise period of time of about 15 minutes and at a temperature of about 30° C., the serum suspected of containing alpha-amylase, with a substrate based upon particulate starch derivatized with determinable groups comprising a reactive dyestuff for the determination of alpha-amylase which does not contain a diazo color system, the substrate being a member selected from the group consisting of superficially cross-linked starch grains which are cross-linked with 0.009 to 0.0027 mole of a difunctional cross-linking agent per 100 g non-swollen starch grains and amylose grains which are cross-linked with 0.02 to 0.07 mole of a difunctional cross-linking agent per 100 g of non-swollen amylose grains, said substrate having a regulated, reduced swellability, said starch and amylose grains having a diameter of from 0.01 to 0.20 mm and measuring said determinable groups as a measure of the initial alpha amylase content.

2. Method as claimed in claim 1, wherein the starch grains have a diameter of from 0.01 to 0.1 mm.

3. Method as claimed in claim 1, wherein the amylose grains have a diameter of from 0.05 to 0.20 mm.

* * * * *